United States Patent
Engel et al.

(10) Patent No.: US 7,896,239 B2
(45) Date of Patent: Mar. 1, 2011

(54) PORTABLE PATIENT CARD, INFORMATION SYSTEM, AND PROCEDURE FOR PATIENT INFORMATION

(75) Inventors: Thomas Engel, Erlangen (DE); Jörg Hassel, Erlangen (DE); Robert Kagermeier, Nürnberg (DE); Frank Roelofs, Lauf (DE); Roland Weiß, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 550 days.

(21) Appl. No.: 11/876,459

(22) Filed: Oct. 22, 2007

(65) Prior Publication Data

US 2008/0099550 A1    May 1, 2008

(30) Foreign Application Priority Data

Oct. 25, 2006   (DE) .................... 10 2006 050 350

(51) Int. Cl.
*G06K 5/00* (2006.01)
(52) U.S. Cl. ................... 235/380; 235/382; 235/487
(58) Field of Classification Search ............ 235/380, 235/382, 382.5, 375, 487
See application file for complete search history.

(56) References Cited

U.S. PATENT DOCUMENTS

2004/0160322 A1* 8/2004 Stilp ................... 340/572.1
2008/0028230 A1* 1/2008 Shatford ................. 713/186
2009/0115581 A1* 5/2009 Forster ................... 340/10.1

FOREIGN PATENT DOCUMENTS

| CN | 1744108 A | 3/2006 |
|---|---|---|
| DE | 10 2005 009 051 A1 | 9/2006 |
| WO | WO 03/027948 A1 | 4/2003 |

OTHER PUBLICATIONS

Ulrike Kihlmann, "Digitales Papier", So funktionieren E-Paper-Displays, pp. 228-233, c't Heft 21 2006.
"Miniature power packs for mobile devices", Fraunhofer magazine 2.2000.
Magnus Båntg, "NOSTOS: A Paper-Based Ubiquitous Computing Healthcare Environment to Support Data Capture and Collaboration", Department of Computer and Information Science, Linköping University, Sweden, AMIA 2003 Symposium Proceedings, pp. 46-50.
European Office Action dated Feb. 19, 2008 for EP 07118427.9-2201 with English translation.
CT Magazine für Computertechnik Ausgage 21/2006, Feb. 10, 2006, Digitales Papier (So funktionieren E-Displays) Seiten 228-233, Ulrike Kuhlmann, Magazine 2006.
German Office Action dated Aug. 6, 2009 for DE 10 2006 050 350.3-53 with English translation.

* cited by examiner

*Primary Examiner*—Karl D. Frech
(74) *Attorney, Agent, or Firm*—Brinks Hofer Gilson & Lione

(57) ABSTRACT

A portable personalized tracker card is provided. The tracker card may be a patient tracker card. The tracker card includes a control unit, a memory for storing personal data, an energy supply unit and an electrochromic display for displaying the personal data.

3 Claims, 3 Drawing Sheets

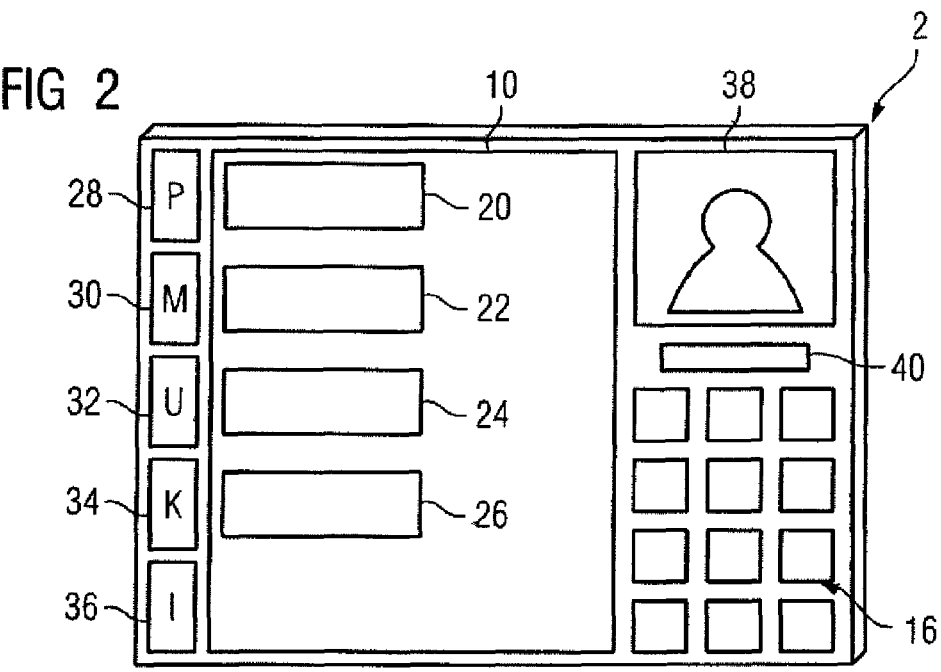
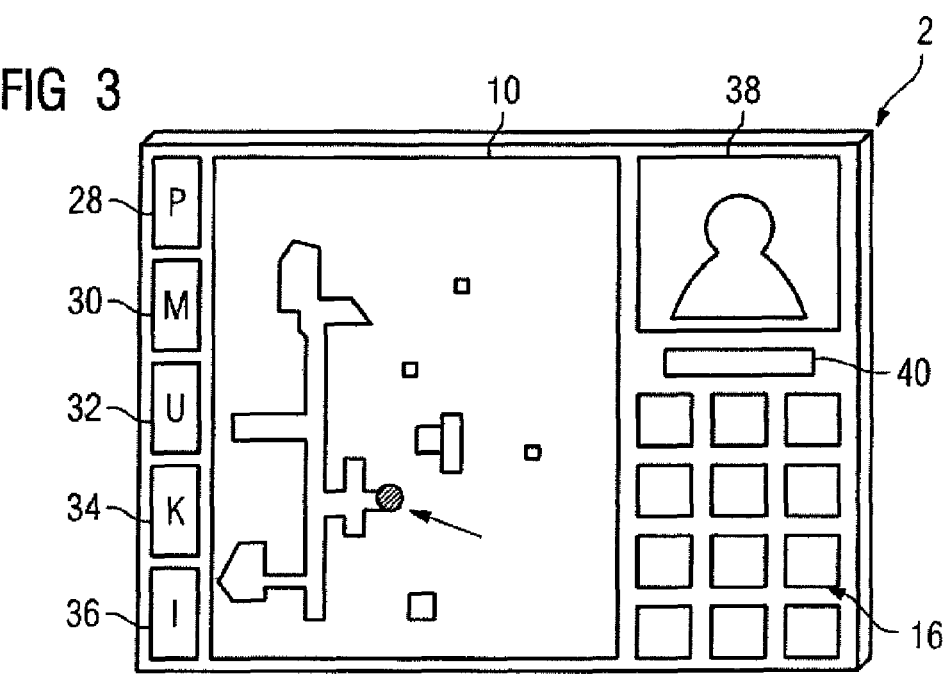

PORTABLE PATIENT CARD, INFORMATION SYSTEM, AND PROCEDURE FOR PATIENT INFORMATION

The present patent document claims the benefit of the filing date of DE 10 2006 050 350.3, filed on Oct. 25, 2006, which is hereby incorporated by reference.

BACKGROUND

The present embodiments relate to a portable patient tracker card, an information system including a number of tracker cards, and a method for outputting and/or forwarding personal data.

An information medium may be used in a work process to simply and quickly output data, such as patient-specific data. For example, in a hospital an examination or treatment of a patient may be accelerated or optimized by making a patient file or tracker card available in proximity to the patient. The treating doctors or nursing staff can view patient data, medication details, examinations to be carried out, or other patient information by using the patient file or tracker card.

In a hospital, patient-specific data is generally stored in a paper-based or electronic patient file. A paper-based patient file may be lost and may not be available (stored) in proximity to the patient, as such files are generally stored in an archive. If there are large quantities of data in the paper-based patient file, it is difficult to find specific information. Electronic patient files are based (stored) on stationary or portable computer systems, which permit fast access to patient data in proximity to the patient but require the use of a complete, expensive and mechanically sensitive device. The device has a high energy requirement and can be used in a mobile manner for a few hours without recharging.

SUMMARY

The present embodiments may obviate one or more limitations or drawbacks inherent in the related art.

In one embodiment, a portable personalized tracker card, such as a patient tracker card, includes a control unit, a memory that stores personal data, an energy supply unit and a display based on a digital paper. The display may be an electrochromic display that displays personal data.

The portable tracker card may be used with digital paper technology, such that the portable tracker card may be low-cost and include small dimensions. Digital paper generally refers to energy-saving displays with a film-type nature. The article "Digitales Papier" (Digital paper) from the magazine "c't—Magazin für Computer Technik", 21/2006, page 228ff provides an overview of different digital paper technologies. An electrochromic display may be a display, such as a color display, which changes color when a direct voltage is applied. The electrochromic display of the tracker card is thin, flexible, light and relatively favorable to produce. An electrochromic display may be produced in all sizes and shapes and include a high contrast. Information displayed on an electrochromic display can be maintained for a relatively long period of time without energy or with little power consumption, as a result of which the energy requirement is low. Personal data is stored in a memory and displayed by a control unit on the electrochromic display. Personal data may include information to identify the person, for example name, data of birth or an internal company identification number. Personal data may include other patient-specific information. The tracker card may store detailed data, such as used, for example, in a hospital as a portable patient tracker card. The detailed data may include examination and/or treatment data, such as medication details or examination appointments. The size of the electrochromic display of the patient tracker card is, for example, DIN format A5 to A4, so that patients can carry them with them, for example, during their hospital stay. Doctors and nursing staff can use the patient tracker card to get a first overview of the patient data and essential hospital history, without requiring an additional device.

In one embodiment, the tracker card includes a communication interface. The communication interface may include the electronic components of the tracker card, which are used to transmit data between the tracker card and further devices. The communication interface may be used to display data stored in the memory. The communication interface may also be used for data transmission between the tracker card and further data devices, so that the stored information can be updated regularly.

In one embodiment, the tracker card includes an RFID transponder, which includes the communication interface. The memory may be a component of an RFID chip. The RFID chip has small dimensions. The RFID chip may be integrated in the patient tracker card without the dimensions of the patient tracker card having to change significantly in the process. An RFID transponder includes, for example, a large memory capacity, low susceptibility to interference, and the possibility of quickly updating and supplementing the data stored on the chip. The RFID chip may store, for example, patient data, building overviews, route descriptions, menus, opening times, or other related data. The patient tracker card may be used to identify the patient and help the patient find their way round the hospital building.

The tracker card may connect to a network adapter for communication, such as wireless communication, with an information system for detailed diagnosis or therapy details. Real-time communication may take place with the hospital's computer-based information system via WLAN or Ethernet when the patient tracker card is coupled to such an external adapter. A wide range of data is available using the network adapter. The locally stored data on the tracker card may be synchronized. The network adapter may be available at each patient station or in each examination room, or may be used by the doctor or nursing staff as a small and robust portable device.

The communication interface may receive position data and the control unit may display the position data. The patient can determine their position in the hospital and find the shortest route using the displayed position data. In hospitals, clinics, or other facilities, patients often find it difficult to find their way around.

The control unit may include a polymer electronic device. A polymer electronic device allows the volume of the patient tracker card to be small. A polymer electronic device may include electrically conducting polymers that are used to establish polytronic applications (e.g. RFID tags, UV filters, actuators, sensors, solar cells, etc.). In contrast to molecular electronics, the information is not processed in individual molecules but in different doped volumes. The polymer electronic device allows economically integrated circuits to be produced in the lower power range on flexible substrates. A polymer electronic device may have a low production cost and a high level of flexibility.

The energy supply unit may be a film battery, having a flat structure and being able to be integrated easily in the tracker card. A film battery may be a solid electrolyte battery developed by the Fraunhofer Institute for Silicon Technology ISIT, as described, for example, in the Fraunhofer Magazine 2.2000.

The energy supply may include solar cells, based on the photovoltaic effect. Photovoltaic solar cells have a broad power spectrum and can use light in the interior of buildings to supply power to the tracker card.

In one embodiment, the tracker card may include a further data input unit. The further data input unit may be a keypad. The keypad may, for example, have a number of keys, with may be used to input and call up (retrieve) information or to navigate on the electronic display.

In one embodiment, the control unit displays a number of menus on the electrochromic display. The menus provide an overview of the data and information stored in the memory. A large amount of data may be classified in this process, and displayed in the form of different menus when called up (displayed). For example, patient data, medication data, or examination appointments may be compiled in individual menus.

In one embodiment, the control unit outputs an appointment reminder, for example, in the form of optical or acoustic signals.

In one embodiment, data is protected. The control unit only displays at least part of the personal data after an ID code has been input. The ID code or PIN number is input by the patient. The ID code or PIN number may be input by the keypad of the tracker card, so that the corresponding data can only be read out by the patient. To release the protected data to further authorized persons, for example, doctors or nursing staff, a read device that reads the RFID transponder or a network adapter may be used. The read device may be used to transmit the data to the hospital's information system.

The personal data of the tracker card may include data about the person and data for the person. The data about the person or patient includes, for example, name, and/or age and all data relating to examinations or treatment of the person or patient. Information for the person or patient relates to information which may be important to the person or patient during their stay in hospital, for example, a route description, menus, or other clinic information.

In one embodiment, an information system may include a number of tracker cards. The information system may be used, for example, in a hospital. The information system includes a number of computers connected in a network. Medical examination and/or treatment devices, which have a computer-based controller, can be connected in the network. The information system may include a number of personalized tracker cards, assigned respectively to the patients in the hospital. The tracker cards may communicate and exchange data with individual devices of the information system or with the information system as a whole by way of the network adapter or by way of the RFID transponder.

The information system may read out the data stored on the tracker card automatically, for example, using the RFID transponder. For example, examination or treatment results of the patient or data required for forthcoming examinations or treatments may be read out by the medical devices. The personal data may be used, for example, to locate a patient within the range of a read/transmit device.

In one embodiment, personal data may be output and/or forwarded using the portable personalized tracker card as described above.

The data may be read in and further processed by the information system. The complete data record is made available quickly and automatically to hospital staff. An examination or treatment may be carried out without patient data having to be input manually or compiled from different sources.

The tracker card may output an appointment reminder, for example, to take medication.

BRIEF DESCRIPTION OF THE DRAWINGS

FIG. 2 shows one embodiment of a tracker card displaying patient data,

FIG. 3 shows the tracker card according to FIG. 1, displaying a route description

DETAILED DESCRIPTION

Figure 1:
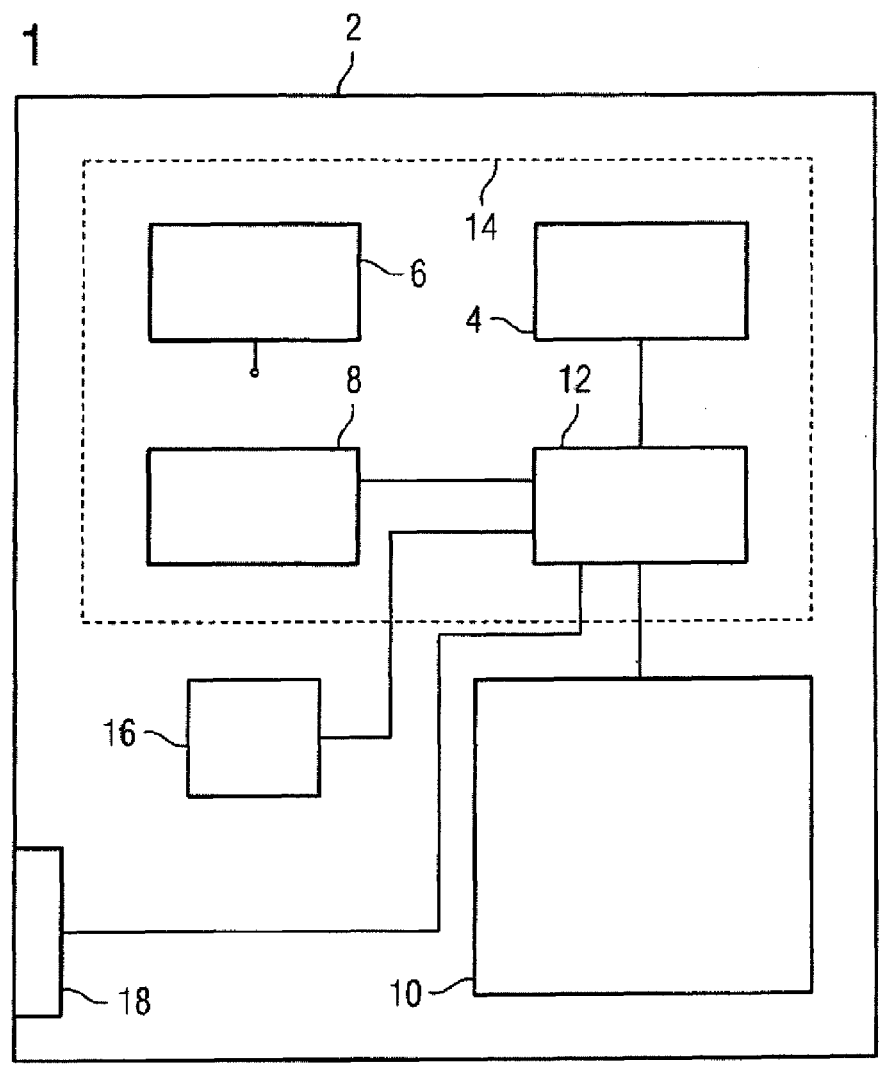
FIG. 1 shows one embodiment of a tracker card.

Identical reference characters have the same significance in the different figures.

FIG. 1 shows a portable tracker card 2. The tracker card 2 may include a memory 4 that stores personal data, an energy supply unit 6, a transmit/receive unit 8, and an electrochromic display 10. The memory 4 may store personal data. The energy supply unit 6 may be a film battery. The energy supply unit 6 may include photovoltaic solar cells (not shown in detail here), disposed for example, on the rear of the tracker card 2. The transmit/receive unit 8 may include a communication interface that communicates with external devices. The electrochromic display 10 may display the personal data. The portable tracker card 2 may include a control unit 12 that activates individual components of the tracker card 2.

In one embodiment, as shown in FIG. 1, an RFID transponder 14 may include the memory 4, the energy supply unit 6, the transmit/receive unit 8 and the control unit 12. The RFID transponder may be a polymer electronic device. The RFID transponder 14 is used to read in and further process the personal data from an RFID read device, which is, for example, part of a diagnostic or therapy system.

The tracker card 2 may include or be affixed to a keypad 16. The keypad 16 may be connected electronically to the farther components of the tracker card 2, such as the control unit 12.

The tracker card 2 and an information system 42 (see FIG. 4) may communicate wirelessly. An interface 10 (e.g. a parallel port or USB port) may be connected to a network adapter 48, by way of which the data transfer takes place between the tracker card 2 and the information system 42 wirelessly.

FIG. 2 shows a patient tracker card 2 for use in a hospital or another medical facility. The patient tracker card 2 includes an electrochromic display 10 and a keypad 16. In this exemplary embodiment, the electrochromic display 10 shows a menu window including a series of four data blocks 20, 22, 24, 26 with alphanumeric characters. The series of four data blocks 20, 22, 24, 26 may include the patient data. For example, block 20 includes the family name of the patient, block 22 the forename, block 24 the date of birth, and block 26 an internal hospital patient identification number.

The menu window including a series of four data blocks 20, 22, 24, 26 may be called up by activating a first menu key P 28 of a menu field, which is disposed next to the electrochromic display 10 and includes the menu keys 30, 32, 34 and 36. Activating the farther menu keys 30, 32, 34 and 36 may change the content of the menu window in the electrochromic display 10. For example, activating the menu key M 30 may cause medication-related information to be output; the menu key U 32 may provide information about the patient's examination appointments; the menu key K 34 may call up a menu window containing comments and information relating to the treatment of the patient and the menu key I 36 may display general information about the hospital, such as a plan of the hospital with the current position of the patient, as shown in FIG. 3.

As shown in FIG. 2 and FIG. 3, the tracker card 2 may include two further information fields 38 and 40 to the right of the electrochromic display 10. For quick visual identification of the patient, the field 38 may include a photograph of the patient, and the field 40 may include the patient's names.

The patient tracker card 2 is flat. For example, the patient tracker card 2 has a thickness of a few millimeters, for example, 1-3 mm. The size of the tracker card 2 is in the range DIN A5 to A4. The patient tracker card 2 may be flexible, sturdy and impact resistant. Patients may carry the patient tracker card 2 with them without any major expenditure of effort during their stay in hospital, so that treating doctors and nursing staff have quick and simple access to patient data at all times.

The tracker card 2 may include an RFID transponder 14. The RFID transponder 14 may be integrated into tracker card 2. The RFID transponder 14 allows the patient data record to be read in, for example, by a read device. The read device may be, for example, part of a diagnostic or therapy system. The diagnostic or therapy system retrieves the complete patient data record with the data required for diagnosis or therapy from a hospital information system 42. Alternatively, the therapy-related data is stored in the memory 4 of the tracker card 2, so that the RFID read device reads it in and forwards it directly to the diagnostic or therapy system.

The tracker card 2 may include a data protection provision. An ID code or PIN number can be input, so that the corresponding data can only be read out by authorized persons. The memory 4 of the tracker card 2 may be divided into at least two different areas, an encrypted and an unencrypted area, with only specific users or user groups being granted access to the data in the encrypted area. The ID code or PIN number is input, for example, by the keypad 16.

The tracker card 2 may include a reminder function. The tracker card 2 outputs optical and/or acoustic signals at specific set times. The patient can be reminded, for example, of an appointment or to take medication.

Figure 4:
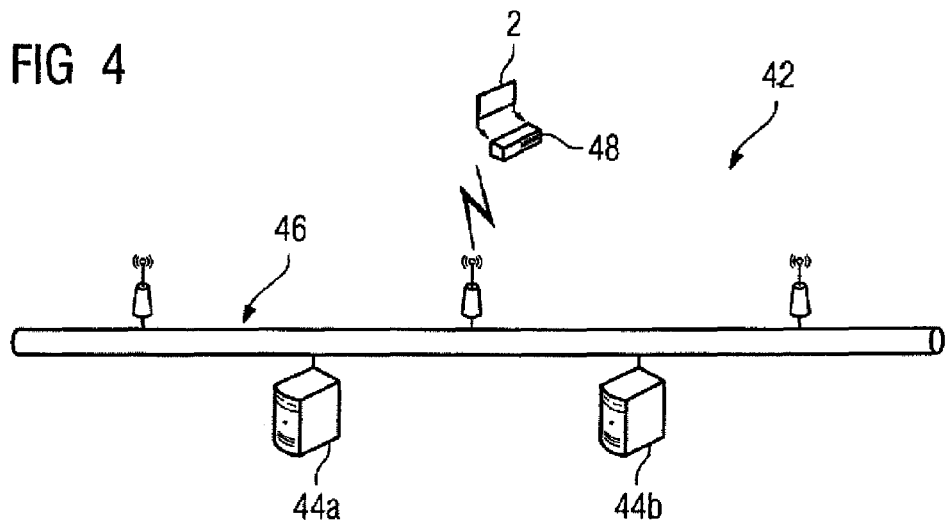
FIG. 4 shows one embodiment of a hospital information system.

In one embodiment, a computer-based information system 42 of the hospital, as shown in FIG. 4, may include a number of patient tracker cards 2. In the exemplary embodiment, as shown in FIG. 4, data is stored on two servers 44a and 44b. The data may be transmitted by an internal network 46, such as a wireless network (WLAN). A patient tracker card 2 may communicate with the information system 42. The patient tracker card 2 is coupled to an external network adapter 48, which allows real-time communication with the servers 44a, 44b or other components of the information system 42 by the wireless network 46. A wide range of information, which is stored on the servers 44a and 44b, is available to the patient. The data stored on the patient tracker card 2 and in the information system 42 may be synchronized. The information system 42 may include the servers 44a, 44b, the tracker cards 2, and further computer-controlled devices, such as diagnostic or therapy systems, for example.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for outputting, forwarding, or outputting and forwarding person-specific data, the method comprising:
    storing the person-specific data in a memory of a portable personalized tracker card comprising a display that includes digital paper,
    displaying the person-specific data stored in the memory on the digital paper of the display, and
    outputting the person-specific data stored in the memory of the portable personalized tracker card to an information system.

2. The method as claimed in claim 1, comprising:
    reading in the person-specific data; and
    processing the person-specific data with the information system.

3. The method as claimed in claim 1, comprising: outputting an appointment reminder using the tracker card.

* * * * *